United States Patent [19]

Harada et al.

[11] Patent Number: 5,169,671
[45] Date of Patent: Dec. 8, 1992

[54] FOOD CONTAINING FRUCTOSE POLYMER

[75] Inventors: Tsutomu Harada; Soji Suzuki; Mika Ikeda; Katsumi Ohata; Fusako Yamanaka, all of Kawasaki, Japan

[73] Assignee: Ajinomoto Co., Inc., Tokyo, Japan

[21] Appl. No.: 753,446

[22] Filed: Aug. 30, 1991

[51] Int. Cl.⁵ .............................................. A23L 1/307
[52] U.S. Cl. .................................... 426/658; 426/565; 426/589; 426/590; 426/570; 426/613; 426/605; 426/652; 426/653; 426/804; 426/603
[58] Field of Search ............... 426/658, 565, 567, 568, 426/569, 570, 571, 605, 589, 613, 652, 653, 590, 804, 603

[56] References Cited

U.S. PATENT DOCUMENTS

| | | | |
|---|---|---|---|
| 4,333,207 | 6/1982 | Heady | 435/94 |
| 4,769,254 | 9/1988 | Mays et al. | 426/658 |
| 4,855,149 | 8/1989 | Pucci et al. | 426/658 |
| 4,859,488 | 8/1989 | Kan et al. | 426/658 |
| 4,877,634 | 10/1989 | Pucci et al. | 426/658 |
| 4,911,946 | 3/1990 | Singer et al. | 426/658 |
| 4,933,191 | 6/1990 | Pucci et al. | 426/658 |
| 4,963,383 | 10/1990 | Nozaki et al. | 426/658 |
| 4,971,814 | 11/1990 | Tomita et al. | 426/658 |
| 4,978,751 | 12/1990 | Biton et al. | 426/658 |
| 5,037,972 | 8/1991 | Jamas et al. | 426/658 |

OTHER PUBLICATIONS

Database WPIL, Derwent Publications, Ltd., London, GB; Database WPIL, Accession No. 90-375690 Week 9050; & U.S.-A-739,304 (U.S. Sec of Agriculture) Jan. 8, 1988. (abstract).

Patent Abstracts of Japan, vol. 13, No. 3, (C-557), Jan. 6, 1989; & JP-A-63216441 (Shimaya) Sep. 8, 1988.

*Primary Examiner*—Jeanette Hunter
*Attorney, Agent, or Firm*—Oblon, Spivak, McClelland et al.

[57] ABSTRACT

There is provided a food and drink having a reduced oil, fat, or sugar content yet retaining good gelation properties and good organoleptic properties, etc. A part of or the whole of gelation materials, low calorie sugars and/or oils and fats is/are replaced with polyfructan.

20 Claims, No Drawings

FOOD CONTAINING FRUCTOSE POLYMER

BACKGROUND OF THE INVENTION

1. Field of the Invention

The present invention relates to a food or drink containing a fructose polymer mainly composed of $\beta$-2,1-bond, hereinafter referred to as "polyfructan", as a substitute for oils, fats, and sugars and having improved gel properties compared with foods containing other oil, fat, or sugar substitutes and a creamy taste and texture equivalent to that derived from oils and fats and a method of producing such a food or drink.

2. Discussion of the Background

In recent years, problems of obesity and hyperlipemia have increased due to excessive consumption of oils, fats, sugars, etc., and decreased consumption of dietary fibers. It has been suggested that certain adult diseases, which are leading causes of death, such as cancer, heart diseases, etc., are associated with excessive consumption of oils, fats, and sugars and decreased consumption of dietary fibers. For these reasons, a low calorie diet has been hitherto prepared by adding sugar alcohols, gum substances, emulsion stabilizers, etc., to foods as substitutes for oils, fats, and sugars.

Examples of low calorie diet foods and methods for preparing the same include: a method for preparing cream or paste for confectioneries or baked goods (Japanese Published Unexamined Patent Application No. 60-66936), soybean milk cream for coffee (Japanese Published Unexamined Patent Application No. 60-153755), low fat, foamable oil in water emulsified fat (Japanese Published Unexamined Patent Application No. 62-22563), low fat cream for whipping and a method for the preparation thereof (Japanese Published Unexamined Patent Application No. 62-118855), low fat spread (Japanese Published Unexamined Patent Application No. 62-232335) and low fat coffee whitener (Japanese Published Unexamined Patent Application No. 63-87942).

In order to substitute a low calorie sweetener having a high degree of sweetness, such as aspartame, for sugar, it is necessary to compensate for the lack of sugar-like volume and texture of the low calorie sweetener by adding a filler comprising a low calorie sugar or gelation material such as polydextrose. However, fillers tend to cause a heavy or "pasty" texture and/or an undesirable taste and flavor in the foods in which they are used.

The substitution of sugar alcohols, gum substances, emulsion stabilizers, etc., for oils and fats tends to dilute the rich taste and flavor of foods. For example, the creamy good-taste and smoothness of ice cream that results when fresh cream is used is seriously damaged when conventional cream substitutes are used. When low calorie materials such as polydextrose of Pfizer Co. or dextrin (Paselli SA-2) of Abebe Co. are used in food as substitutes for oils and fats, the food acquires a sour, pungent, or astringent taste or a floury flavor. These conventional low calorie materials used to reduce the amount of sugar or to increase bulk and texture or to create a creamy taste and texture fail to provide adequate taste and flavor. In addition, these materials tend to detrimentally affect such physical properties of food as shape retention, extensibility, stringiness, etc.

SUMMARY OF THE INVENTION

Accordingly, one object of this invention is to solve the defects associated with conventional oil and fat substitutes, low calorie sugars, gelation materials, and thickening agents, by providing a material which exhibits good gel properties and good organoleptic characteristics such as creamy taste and texture without any adverse affects on flavor, taste, and texture when incorporated into foods or drinks.

A further object of this invention is to provide a material that may be used with a low calorie sweetener having a high degree of sweetness, as a substitute for sugar, to compensate for the lack of sugar-like volume and texture of the low calorie sweetner.

A further object of this invention is to provide a material that may be used with water, milk, or a mixture of water and milk as an oil and fat substitute.

A further object of this invention is to provide a material that may be used as a substitute for thickening agents and gelation materials.

A further object of this invention is to provide a food or drink having reduced sugar, oil, or fat content yet retaining good gel properties and good organoleptic characteristics of taste and texture by substituting a material for oils and fats, conventional oil and fat substitutes, thickening agents, gelation materials, and low calorie sugars in foods or drinks.

A further object of this invention is to provide a method of producing a food or drink having reduced sugar, oil, or fat content yet retaining good gel properties and good organoleptic characteristics of taste and texture by substituting a material for oils and fats, conventional oil and fat substitutes, thickening agents, gelation materials, and low calorie sugars in foods or drinks.

According to the present invention, there is thus provided a food or drink containing a fructose polymer mainly composed of $\beta$-2,1-bond and a method of producing a food or drink with reduced oil, fat, and sugar content yet retaining good gelation properties and good organoleptic properties such as taste, texture, and flavor comprising substituting, wholly or partially, a fructose polymer mainly composed of $\beta$-2,1-bond for oils and fats, oil and fat substitutes, gelation materials, thickening agents, and low calorie sugars.

DETAILED DESCRIPTION OF THE PREFERRED EMBODIMENTS

As a result of extensively investigating a solution to the problems described above, the present inventors have found that by incorporating polyfructan composed mainly of $\beta$-2,1-bond in foods as a substitute for oils, fats, low calorie sugars, thickening agents, and gelatin materials, it is possible to provide a food having good organoleptic characteristics such as creamy taste and texture and good gelation without adversely affecting flavor, taste, and texture as with conventional oil and fat substitutes, gelation materials, thickening agents, and low calorie sugars.

The polyfructan used in the present invention is mainly composed of $\beta$-2,1-bond and has a molecular weight in the range of 2,000 to 20,000,000, preferably in the range of 10,000 to 15,000,000. A polyfructan containing $\beta$-2,6-bond as a branched chain may also be effective.

To produce polyfructan, it is conventional to use a method for incubating the conidium of *Aspergillus sydowi* and sugar (Kawai et al., Agric. Biol. Chem., 37, 2111, 1973). The polyfructan may also be produced by other methods, such as using fructose transferase derived from yeast, *Aspergillus oryzae, Aspergillus niger, Aureobasidium pullulans,* etc., and sugar (such as sucrose) or inulin (derived from Jerusalem artichoke, etc.)

As described hereinabove, the polyfructan used in the present invention is known. Because inulin is difficult to digest and because it helps Bifidobacterium proliferate in the intestine, it is expected to be effective in relieving constipation. In addition, it may be applied to a patient with diabetes because it does not increase blood sugar even in a blood sugar load test, and it reduces the triglycerides and the cholesterol level in the blood and liver. It is assumed that polyfructan would have similar effects. Polyfructan can be applied in the form of a powder or liquid to such foods as breads, biscuits, etc. (Japanese Published Unexamined Patent Application No. 61-87797).

However, the characteristics of polyfructan are unknown and the application of polyfructan to specific foods because of its physical properties, functional characteristics, etc., is as yet undeveloped.

The present inventors have investigated the properties of polyfructan while trying to develop an industrial process for preparing it. As a result, they found that an aqueous paste composition of polyfructan has a texture similar to oils and fats. Furthermore, by substituting this composition for liquid oils and solid fats such as fresh cream, cream cheese, butter, salad oil, etc., in various cooked and processed food, the number of calories in the resulting food are greatly reduced without the adverse effects on flavor, taste, texture, etc., associated with conventional oil and fat substitutes. For example, in foods using fresh cream, almost 70% can be replaced with the polyfructan paste without sacrificing the creamy texture, the rich taste, or the flavor of fresh cream. Furthermore, the properties of the fresh cream, such as the creamy texture and rich taste and flavor, are not damaged.

By substituting gelation materials, thickening agents, and low calorie sugars such as polydextrose, etc., with polyfructan or by combining these materials with polyfructan, properties such as increased viscosity, tough texture, sour pungent taste, etc., can be markedly improved. Thus, it is possible to approximate the properties of sugar, e.g., volume, water retention, moisturization, etc., by using the polyfructan in combination with a sweetener having a high degree of sweetness, such as aspartame. Such properties of sugar could not be adequately compensated for by using the low calorie sugars described above in combination with a sweetener having a high degree of sweetness. Accordingly, polyfructan provides the necessary mass and volume as a bulking agent when combined with a sweetener having a high degree of sweetness in formulating a table sweetener or a sweetener for use in other food.

Foods incorporating polyfructan may also contain suitable amounts of other components without any detrimental effects. For example, such other components include a sweetener having a high degree of sweetness, a coloring material, a pigment, an emulsifier, a gum substance, protein, a flavor, a spice, etc.

Polyfructan may be used in the form of a powder but its use as a fluid is preferred. That is, polyfructan is preferably dispersed in water, milk, other raw materials of a food or drink, or mixture thereof, in 10 to 40% (w/w) to form a paste. The hardness of the paste can be adjusted by controlling the amount of polyfructan in water, milk, other raw materials of a food or drink, or mixture thereof so as not to damage the physical properties of the foods prepared.

Oils and fats may be wholly substituted with a form of polyfructan, e.g., an aqueous paste. However, a preferred degree of substitution is 20 to 70% by weight based on the oils and fats.

Where gelation materials or thickening agents such as gelatin, animal or vegetable protein gel including albumen or yolk, polysaccharides such as pectin, carrageenan, xanthane gum, guar gum and other gum substances, etc., are substituted with polyfructan, the degree or ratio of substitution may be varied depending upon the gelation materials or thickening agents to be substituted. The determination of the optimum ratio of polyfructan to gelation materials or thickening agents depends upon the desired degree of gelation which is understood from an index of gel properties associated with texture such as gel intensity, strain, etc.

The polyfructan of the present invention has a low viscosity. Its dispersion is spreadable, smooth and creamy with good melt in the mouth characteristics yet remains tasteles and free of the pungent or bitter taste and floury flavor often associated with polysaccharides. Therefore, when incorporated into the foods described above, it became possible to reinforce the creamy taste and texture that was impossible with other gum substances or polysaccharides. That is, the polyfructan can reinforce a creamy taste and texture without damaging the taste and texture inherently in the food.

Furthermore, the gelation materials and the like release water with passage of time when they are incorporated into meats such as ham, sausage, etc. The polyfructan of the present invention is advantageous over these previous gelation substitutes in that it helps prevent the release of water.

Specific examples applying the polyfructan to foods and the preferred properties are explained in more detail by referring to the examples below. Other features of the invention will become apparent in the course of the following description of exemplary embodiments which are given for illustration of the invention and are not intended to be limiting thereof.

Obviously, numerous modifications and variations of the present invention are possible in light of the above teachings. It is therefore to be understood that within the scope of the appended claims, the invention may be practiced otherwise than as specifically described herein.

EXAMPLES

Example 1

Low Calorie Mayonnaise

Following the formulation shown in Table I, low calorie mayonnaise was prepared by substituting an aqueous paste of polyfructan for corn salad oil. As a control, mayonnaise was prepared using the whole amount of corn salad oil. The 4 test samples were evaluated by 12 panel members on the basis of appearance, agreeability to the palate, meltability on the tongue, smooth swallowing, flavor, taste, and other properties. The samples were judged on a scale of 1 to 10. A score of 10 indicates a rating of very favorable, a score of 5 indicates a rating equivalent to the control, and a score of 1 indicates a rating of very unfavorable.

The results are shown in Table 1. Among low calorie mayonnaise samples, mayonnaise (D) in which 20% polyfructan aqueous paste was substituted for 67% of the corn salad oil and mayonnaise (A) in which 25% polyfructan aqueous paste was substituted for 33% of the corn salad oil were good in agreeability to the palate, meltability on the tongue and smooth swallowing, and showed reduction in unpleasant oily smell, mild sour taste and salty taste. These samples were judged, as the total scoring, to be almost equivalent to the control.

Example 2 Low Calorie Dressing

Following the formulation shown in Table 3, low calorie dressing was prepared by substituting an aqueous paste of polyfructan for corn salad oil. As a control, low calorie dressing was prepared using the whole amount of corn salad oil. The 3 test samples were evaluated by 6 panel members on the basis of appearance, agreeability to the palate, meltability on the tongue, smooth swallowing, flavor, taste, and other properties. The samples were judged on a scale of 1 to 10. A score of 10 indicates a rating of very favorable , a score of 5 indicates a rating equivalent to the control, and a score of 1 indicates a rating of very unfavorable.

The results are shown in Table 4. Among low calorie dressing samples, dressing (C) in which 20% polyfructan aqueous paste was substituted for 67% of the corn salad oil and dressing (A) in which 20% polyfructan aqueous paste was substituted for 33% of the corn salad oil were good in agreeability to the palate, meltability on the tongue and smooth swallowing, and showed reduction in unpleasant oily smell, mild sour taste and salty taste. These samples were judged, as the total scoring, to be almost equivalent to the control.

Example 3

Low Calorie Whipped Cream

Following the formulation shown in Table 5, low calorie whipped cream was prepared by substituting an aqueous paste of polyfructan and polydextrose for fresh cream. As a control, whipped cream was prepared using the whole amount of fresh cream. The 2 test samples were evaluated by 8 panel members on the basis of appearance, agreeability to the palate, meltability on the tongue, smooth swallowing, flavor, taste and other properties.

The whipped cream (A) in which polyfructan was substituted for 50% of the fresh cream maintained the creamy texture and rich taste and flavor of fresh cream, indicating a good taste property. Separation of the whipped cream (A) prepared using the polyfructan occurred only with excessive frothing upon whipping. Therefore, it is believed that polyfructan tends to have an action in preventing separation. Whipped cream (B) prepared using polydextrose showed a considerably weaker rich taste and flavor of fresh cream and possessed a strong rough, sour, and astringent taste.

Example 4

Low Calorie Bavarois

Following the formulation shown in Table 6, low calorie bavarois was prepared by substituting an aqueous paste of polyfructan for fresh cream. As a control, bavarois was prepared using the whole amount of fresh cream. The 2 test samples were evaluated by 6 panel members on the basis of appearance, agreeability to the palate, meltability on the tongue, smooth swallowing, flavor, taste and other properties.

Bavarois (A) in which 25% polyfructan aqueous paste was substituted for half the fresh cream showed good meltability on the tongue and pleasant smoothness on the tongue. Furthermore, bavarois (A) in which 25% polyfructan aqueous paste was substituted for half the fresh cream retained the rich taste and flavor inherently possessed by fresh cream. Bavarois obtained using a paste of the polyfructan in milk showed similar results.

Example 5

Low Calorie Chocolate Cream

Following the formulation shown in Table 7, low calorie chocolate cream was prepared by substituting an aqueous paste of polyfructan for fresh cream. As a control, chocolate cream was prepared using the whole amount of fresh cream. The 3 test samples were evaluated by 12 panel members on the basis of appearance, agreeability to the palate, meltability on the tongue, smooth swallowing, flavor, taste, and other properties. The samples were judged on a scale of 1 to 10. A score of 10 indicates a rating of very favorable , a score of 5 indicates a rating equivalent to the control, and a score of 1 indicates a rating of very unfavorable.

The results are shown in Table 8. Chocolate cream (A) in which 20% polyfructan was substituted for ⅓ of the fresh cream and chocolate cream (B) in which 20% polyfructan was substituted for ⅔ of the fresh cream were good in meltability on the tongue and mild. In fact, they received a more favorable total score than the control.

Example 6

Low Calorie Souffle Gras

Following the formulation shown in Table 9, low calorie souffle gras was prepared by substituting an aqueous paste of polyfructan for fresh cream. As a control, souffle gras was prepared using the whole amount of fresh cream. The 2 test samples were evaluated by 6 panel members on the basis of appearance, agreeability to the palate, meltability on the tongue, smooth swallowing, flavor, taste and other properties.

Souffle gras (A) in which 20% polyfructan was substituted for half the fresh cream retained the pleasant flavor, rich taste and texture of fresh cream. On the other hand, souffle gras (B) prepared using Paselli SA-2, which is the oil and fat substitute dextrin of Abebe Co., showed poor fresh cream flavor and texture and possessed a powdery flavor.

Example 7

Low Calorie Cheese Paste

Following the formulation shown in Table 10, low calorie cheese paste was prepared by substituting an aqueous paste of polyfructan for cream cheese. Evaluation was made in a similar manner.

Cheese paste (A) in which 25% polyfructan was substituted for half the cream cheese retained the flavor of cream cheese, showed good meltability on the tongue and good spreadability on bread, etc., and possessed smooth texture. Cheese paste (B) in which 25% polyfructan paste was substituted for ¾ of cream cheese showed a good texture, although its flavor was somewhat weak.

Example 8

Low Calorie Rare Cheese Cake

Following the formulation shown in Table 11, low calorie rare cheese cake was prepared by substituting an aqueous paste of the polyfructan for fresh cream and was evaluated similarly to previous examples.

Rare cheese cake (A) in which 20% polyfructan paste was substituted for half the fresh cream showed good agreeability to the palate and smooth texture and was tasty. Rare cheese cake (B) prepared using Paselli SA-2, which is the oil and fat substitute dextrin of Abebe Co., had a powdery and foreign taste, and was not thus favorable.

Example 9

Low Calorie Butter Cream

Following the formulation shown in Table 12, low calorie butter cream was prepared by substituting an aqueous paste of polyfructan for salt-free butter and was evaluated similarly to previous examples.

Butter cream (A) in which 25% polyfructan paste was substituted for half the salt-free butter retained the flavor of butter cream, was free of collapse in shape due to elevated temperature, namely, good shape retention and was tasty. Butter cream (B) in which polydextrose of Pfizer was substituted for half the salt-free butter showed a weak flavor of butter cream and showed a strong sour, rough and astringent taste.

Example 10

Low Calorie Baked Cheese Cake

Following the formulation shown in Table 13, low calorie baked cheese cake was prepared by substituting an aqueous paste of the polyfructan for fresh cream or cream cheese. Baking conditions were at 180° C. for 50 minutes and then at 150° C. for 20 minutes. As a control, baked cheese cake was prepared using the whole amount of fresh cream and cream cheese. The 4 test samples were evaluated by 6 panel members on the basis of appearance, agreeability to the palate, meltability on the tongue, smooth swallowing, flavor, taste and other properties. The cake samples all possessed a good taste, as shown in Table 14.

Example 11

Low Calorie Madeleine

Following the formulation shown in Table 15, low calorie madeleine was prepared by substituting an aqueous paste of polyfructan for salt-free butter. Baking conditions were at 180° C. for 30 minutes. As a control, madeleine was prepared using the whole amount of salt-free butter. The 4 test samples were evaluated by 8 panel members on the basis of appearance, texture, taste and flavor. Madeleine in which polyfructan was substituted for 33% of salt-free butter retained a flavor of butter and was equivalent to the control in appearance and texture, as shown in Table 16. Moist and smooth texture were imparted to the madeleine, indicating a good taste.

Example 12

Low Calorie Bread

Following the formulation shown in Table 17, low calorie bread was prepared by substituting an aqueous paste of polyfructan for shortening. For the preparation, automatic home bakery SD-BT3 manufactured by Matsushita Electronic Industry Co., Ltd. was used.

Bread prepared using the whole amount of shortening was made as a control. A taste evaluation of 2 test samples was performed in a manner similar to that described above. As the result, the samples all showed a good taste, as shown in Table 18.

Example 13

Low Calorie American Pastry

Following the formulation shown in Table 19, low calorie American pastry was prepared by substituting an aqueous paste of polyfructan for salt-free butter. Baking conditions were at 160–170° C. for 30 minutes. American pastry prepared using the whole amount of salt-free butter was made as a control. A taste evaluation of test samples (A) and (B) was performed in a manner similar to that described above by 10 panel members.

A crispy texture which is important for pie increased in both samples, without changing taste and flavor. The samples showed good taste. In addition, the samples formed a color only with difficulty when backed.

Example 14

Low Calorie Brioche

Following the formulation shown in Table 20, low calorie brioche was prepared by substituting an aqueous paste of polyfructan for shortening. For the preparation, automatic home bakery SD-BT3 manufactured by Matsushita Electronic Industry Co., Ltd. was used. Brioche prepared using the whole amount of shortening was made as a control. A taste evaluation of 2 test samples was performed in a manner similar to that described above. The two samples showed improved meltability on the tongue and chewiness and showed a favorable decrease in the oily smell of shortening.

Example 15

Low Calorie Doughnuts

Following the formulation shown in Table 21, low calorie doughnuts were prepared by substituting an aqueous paste of polyfructan for shortening. Frying was performed at 160° C. for 30 minutes. A taste evaluation was performed in a manner similar to that described above. As compared to the control prepared using the whole amount of shortening, the samples showed an increase in elasticity, a good consumer acceptance in texture and were favorably free of an unpleasant oily flavor.

Example 16

Low Calorie Corn Potage Soup

Following the formulation shown in Tables 22 and 23 low calorie corn potage soup was prepared by substituting an aqueous paste of polyfructan for fresh cream. Corn potage soup prepared using the whole amount of fresh cream was made as a control. Sensory evaluation of test samples (A) and (B) was performed in a similar manner by 6 panel members. The samples (A) and (B) both had a texture, taste and flavor similar to the control, retained the fresh cream flavor of the control, and were highly tasty with body texture.

Example 17

Low Calorie Margarine

Following the formulation shown in Table 24, low calorie margarine was prepared by substituting an aqueous paste of polyfructan for the margarine blend oil (soybean oil +hydrogenated oil and fat). Margarine prepared using the whole amount of margarine blend oil was made as a control. Sensory evaluation of test samples (A) and (B) was performed in a similar manner. As the result, the samples (A) and (B) both had an improved meltability on the tongue, imparted spreadability and were favorably tasty, as compared to control.

Example 18

Yogurt Beverage

Yogurt beverage shown in Table 25 was prepared as samples in a conventional manner.

Sensory evaluation of A and B was performed by a panel of 20 individuals. B was preferred by a ratio of 3:1. In the polydextrose group of A, a strong pungent, astringent, rough and bitter taste was noted. B had a lesser pungent, astringent and rough taste and was judged good.

Example 19

Soup

Soup shown in Table 26 was prepared in a conventional manner. (A) showed a strong sour and bitter taste. (B) showed good balance in taste.

Example 20

Cocoa

Cocoa shown in Table 27 was prepared. (A) prepared using polydextrose showed a strong sour and rough taste.

A sensory evaluation of (A) and (B) was performed by a panel of 20 individuals. By a ratio of 18:2, (B) prepared using polyfructan showed good taste. (B) using polyfructan was preferred.

Example 21

Yogurt Beverage

Following the formulation described below, yogurt beverage samples were prepared using polyfructan.

| Formulation (unit: gram) | |
|---|---|
| Plain yoghurt: | 60.0 |
| Water: | 40.0 |
| Polyfructan: | 8.0 |
| Aspartame | 0.032 |

Yogurt beverage samples prepared by the above formulation were comparable in texture with the control group prepared using 8.0 g of sugar, indicating a favorable taste equivalent to the control group. To examine the physical properties, the degree of water release was determined after centrifugation. When 5 ml of yogurt was used, 3 ml of water release was noted in the control group, whereas in the formulation group, water release was as small as 0.7 ml, indicating the effect of polyfructan in preventing water release.

The foregoing results reveal that when a sweetener having a high degree of sweetness is used in a milk beverage such as a yogurt beverage, lactic acid beverage, etc., the bulk of polyfructan not only reinforces body texture (bulk and space) and imparts organoleptic properties equivalent to those of sugar but it can also be expected to exhibit effect in preventing water release. Among ordinary gum substances, guar gum, which is known to have the effect of preventing water release fails to reinforce body texture (bulk and space). By using polyfructan, the both effects can be exhibited at the same time.

Example 22

Improvement in Shape Retention Property of Low Calorie Ice Cream

Following the formulation shown in Table 28, ice cream was prepared.

In the group (B) using polydextrose, shape was collapsed in about 10 minutes after standing at room temperature, and in the control group (A), shape was collapsed in about 30 minutes.

On the other hand, the group (C) using polyfructan retained its shape even after standing at room temperature for an hour.

Example 23

Sponge Cake

Three sponge cakes shown in Table 29 were prepared. There were no difference among control (A), (B) and (C) in taste and texture immediately after baking.

However, 2 to 3 days after baking, sponge cake (B) baked using polydextrose showed a sticky texture.

Sponge cake (C) baked using the polyfructan retained its texture soon after baking even 3 days after and showed more elasticity and a smoother texture than control (A).

Example 24

Sponge Cake

Using the polyfructan, sponge cake samples were prepared in the following formulation:

| Formulation (unit: gram) | |
|---|---|
| Polyfructan: | 6.0 |
| Water: | 10.0 |
| Sugar: | 20.0 |
| Yolk: | 45.0 |
| Albumen: | 60.0 |
| Milk: | 10.0 |
| Wheat flour: | 40.0 |
| Butter: | 10.0 |
| Aspartame | 0.1 |

Sponge cake prepared by the above formulation showed puffing ability in its appearance similar to the control group in a conventional formulation in which 40.0 g of sugar was used and no polyfructan, aspartame, or water were used. In texture, the sponge cake showed less stickiness and light agreeability to the palate.

The foregoing results reveal that when polyfructan is used with an amount of sugar less than that used in the control group, the polyfructan not only compensates for the solid content in an amount corresponding to the reduced amount of sugar but also exhibits a puffing effect similar to sugar, i.e., a shape retention effect. According to the present method, it is possible to supplement the shape retention effect when a sweetener having a high degree of sweetness, such as aspartame, etc., is used in cake-like foods, e.g., sponge cake, castilla, pound cake, Karukan (sweetened jelly of yam and rice flour), etc., prepared by whipping egg albumen, etc., and fixing the foam to impart a texture thereto.

Example 25

Cookie

Using polyfructan, cookie samples were prepared in the following formulation.

| Formulation (unit: gram) | |
| --- | --- |
| Polyfructan: | 10.0 |
| Water: | 5.0 |
| Butter: | 25.0 |
| Sugar: | 10.0 |
| Yolk: | 15.0 |
| Wheat flour: | 50.0 |
| Aspartame | 0.05 |

Cookies prepared by the above formulation showed puffing ability and an appearance somewhat better than a control group in which a conventional formulation utilizing 10.0 g of sugar was used but no polyfructan, aspartame, or water was used, although baked a little longer. In texture, the cookie showed a moist and soft taste and crispy and pleasant roughness in combination.

The foregoing results reveal that when polyfructan is used, it is possible to improve the puffing ability of baked cakes such as cookie, sable, biscuit, etc., and at the same time, impart a crispy and soft texture thereto.

Example 26

Lacto-ice Cream

Using polyfructan, lacto-ice cream samples were prepared in the following formulation.

| Formulation (unit: gram) | |
| --- | --- |
| Coconut oil: | 30.0 |
| Skimmed milk: | 40.0 |
| Sugar: | 75.0 |
| Gum substance: | 3.0 |
| Monoglyceride: | 3.0 |
| Vanilla essence: | 2.0 |
| Water: | 772.0 |
| Polyfructan | 75.0 |
| Aspartame | 0.44 |

Lacto-ice cream samples prepared by the above formulation showed no difference in appearance from the control group prepared by a conventional formulation in which 150 g of sugar was used but neither polyfructan nor aspartame was used. In texture, the lacto-ice cream showed good meltability on the tongue and was smooth. In physical properties, the lacto-ice cream molded into a cylinder having a diameter of 2.0 cm and a length of 3.0 cm was put at a temperature of 20° C. and a time until the ice melted out was visually measured. In the control group, the ice cream lost its shape in 35 minutes, whereas the ice cream in the test group having the formulation described above lost its shape in 55 minutes. In the control group, water release was caused but no water release was noted in the test group.

The foregoing results reveal that when the polyfructan is used, smoothness and meltability on the tongue similar to sugar are imparted, namely, growth of ice crystal is prevented and a shape retention property that when put at room temperature, its shape is retained over a long period, is also imparted. According to the present method, it is expected to reinforce a body texture and smoothness when a sweetener having a high degree of sweetness, such as aspartame, etc., is used in cakes such as lacto-ice cream, ice milk, sherbet, etc., which are prepared by ice crystals.

Example 27

Jam

Polyfructan was substituted for a half (A) and all (B) of the weight of sugar, respectively. Following the formulation (unit: gram) shown in Table 30, 3 kinds of jams were subjected to organoleptic examination on physical properties (smoothness and stickiness) by 10 panel members with respect to the products immediately after preparation and after storage. Evaluation was performed by comparing the test groups (A) and (B) shown in Table 30 with the control group in which sugar was used. The results are as follows.

Criterion for evaluation:
Score 0 ... worse than the control group
Score 2.5 ... somewhat worse than the control group
Score 5.0 ... same as the control group
Score 7.5 ... somewhat better than the control group
Score 10.0 ... better than the control group Immediately after the preparation, there was almost no difference in the physical properties and the scoring was as shown in Table 31. After storage, however, sugar crystals were precipitated in the control group but no crystal was precipitated in the test group, which is reflected by the scoring shown in Table 32.

In this case, the jam was characteristic of smoothness being imparted due to no precipitation of crystals, no increase in viscosity caused by a conventional crystallization prevention agent, e.g., dextrin, because of low viscosity of the polyfructan and softness inherent to jam being retained without becoming hard, and because of good water retention property.

The foregoing results reveal that when the polyfructan is used in jam, it is possible to prevent crystallization during storage, without affecting other properties of jam, e.g., viscosity, hardness, etc.

According to the present method, it is possible to use the fructose polymer in food such as jam, marmalade, fruit sauce, etc., wherein sugar is used as a body, together with a sweetener having a high degree of sweetness.

Example 28

Jelly

The polyfructan was substituted for 50% (A) and 25% (B) of the weight of sugar respectively. Following the formulation (unit: gram) shown in Table 33, 2 jelly samples were prepared.

The jelly samples prepared in the formulation described above showed no difference in appearance and texture, from the control group prepared in a conventional formulation in which 40 g of sugar was used but neither polyfructan nor aspartame was used.

The foregoing results reveal that by using polyfructan, it is possible to prepare dietary fiber-reinforced jelly having a good appearance and texture equivalent to jelly prepared using sugar.

When polyfructan is used with a dietary fiber, it is possible to add dietary fiber in a higher concentration than when conventional gum substances such as pectin, etc., are used due to its low viscosity when formed in a solution. It is also possible to impart organoleptic properties of sugar, e.g., hardness, smoothness, meltability on the tongue, and the like, to jelly.

Example 29

Gel

Using the polyfructan derived from *Aspergillus sydowi*, agar and starch gel were prepared in the following formulation. Breaking strength and deformation were determined by a rheometer. A size of the gel was 3 cm in diameter and 3 cm in width and a spherical plunger of 10 mm was used.

| Formulation: | |
|---|---|
| Agar gel: agar powder | 3% |
| *Aspergillus sydowi*-derived polyfructan | 1% |
| In the control group, 3% of agar powder alone was used. | |
| Starch gel: corn starch | 20% |
| *Aspergillus sydowi*-derived polyfructan | 7% |
| In the control group, 20% corn starch alone was used. | |
| Breaking strength and deformation were as follows. | |
| Agar gel: | |
| breaking strength | 433 g/cm$^2$ (637 g/cm$^2$) |
| deformation | 0.6 cm (0.5 cm) |
| Starch gel: | |
| breaking strength | 36 g/cm$^2$ (166 g/cm$^2$) |
| deformation | 0 cm (0.8 cm) |

Data within parenthesis indicate the control group.

As described above, softness was imparted to the gel by adding the polyfructan.

Example 30

Custard Pudding

Using the polyfructon derived from *Aspergillus sydowi*, custard pudding samples were prepared in the following formulation.

| Formulation (unit: gram) | |
|---|---|
| *Aspergillus sydowi*-derived polyfructan: | 25.0 |
| Granulated sugar: | 25.0 |
| Egg: | 100 |
| Milk: | 240 |
| Aspartame: | 0.125 |
| Vanilla essence: | 0.1 |

The custard pudding samples prepared in the formulation described above showed no pore in appearance but were smooth and possessed more creamy taste and texture and was meltable on the tongue, as compared to the control group in which 50 g of sugar was used.

Example 31

Rare Cheese Cake

Using the polyfructan derived from *Aspergillus sydowi*, rare cheese cake samples were prepared in the following formulation.

| Formulation (unit: gram) | |
|---|---|
| Cream cheese: | 150 |
| *Aspergillus sydowi*-derived polyfructan: | 10 |
| Milk: | 40 |
| Granulated sugar: | 20 |
| Lemon juice: | 10 |
| Gelatin: | 5 |

| -continued | |
|---|---|
| Formulation (unit: gram) | |
| Water: | 50 |

The rare cheese cake samples prepared in the formulation described above showed no difference in appearance and were creamy and meltable on the tongue and smooth, as compared to the control group in which 20 g of sugar was used. By adding the polyfructan, the creamy texture was reinforced.

Example 32

Chocolate Mousse

Using the polyfructan derived from *Aspergillus sydowi*, chocolate mousse samples were prepared in the following formulation.

| Formulation (unit: gram) | |
|---|---|
| Chocolate: | 70 |
| Yolk: | 20 |
| *Aspergillus sydowi*-derived polyfructan: | 20 |
| Milk: | 100 |
| Gelatin: | 10 |
| Fresh cream: | 50 |
| Albumen: | 50 |
| Granulated sugar: | 20 |
| Aspartame: | 0.05 |

The chocolate mousse samples prepared in the formulation described above showed no difference in appearance and were smooth and agreeable to the palate, more creamy and meltable on the tongue and rich, as compared to the control group in which 40 g of sugar was used.

Example 33

Wine Cream

Using the polyfructan derived from *Aspergillus sydowi*, wine cream samples were prepared in the following formulation.

| Formulation (unit: gram) | |
|---|---|
| Corn starch: | 5 |
| White wine: | 50 |
| Gelatin: | 5 |
| Cream cheese: | 150 |
| *Aspergillus sydowli*-derived polyfructan: | 25 |
| Milk: | 75 |
| Lemon juice: | 50 |
| Fresh cream: | 50 |
| Albumen: | 50 |
| Aspartame: | 0.1 |

The wine cream samples prepared in the formulation described above showed no difference in appearance and were smooth and more creamy and meltable on the tongue, as compared to the control group in which 25 g of sugar was used.

Example 34

Bavarois

Using the polyfructan derived from *Aspergillus sydowi*, bavarois samples were prepared in the following formulation.

| Formulation (unit: gram) | |
| --- | --- |
| *Aspergillus sydowi*-derived polyfructan: | 38 |
| Milk: | 135 |
| Fresh cream: | 55 |
| Yolk: | 20 |
| Gelatin: | 6 |
| Aspartame: | 0.19 |
| Water: | 35 |
| Vanilla essence: | 0.1 |

The bavarois samples prepared in the formulation described above showed no difference in appearance and were smooth and more creamy and meltable on the tongue, as compared to the control group in which 38 g of sugar was used.

Example 35

Ice Cream

Using the polyfructan derived from *Aspergillus sydowi*, ice cream samples were prepared in the following formulation.

| Formulation (unit: gram) | |
| --- | --- |
| Gelatin: | 3 |
| Water: | 15 |
| Milk: | 200 |
| Yolk: | 30 |
| Liquor: | 15 |
| Sugar: | 25 |
| Aspartame: | 0.14 |
| Fresh cream: | 100 |
| *Aspergillus sydowi*-derived polyfructan: | 25 |

The ice cream samples prepared in the formulation described above showed no difference in appearance and were smooth and more creamy in meltability on the tongue, as compared to the control group in which 1 g of guar gum was used. By adding the polyfructan, the creamy texture was reinforced.

Example 36

With respect to various desserts prepared in Examples 30 through 35, organoleptic evaluation was performed by 9 panel members on a creamy texture such as softness, smoothness, spreadability, etc., and the total creamy taste and texture. As a control, there were provided samples prepared in a conventional formulation in which no polyfructan was used.

Criterion for the evaluation is as follows.
Score 0 ... worse than the control group
Score 2.5 ... somewhat worse than the control group
Score 5.0 ... same as the control group
Score 7.5 ... somewhat better than the control group
Score 10.0 ... better than the control group

Results

As shown in Table 34, it was confirmed in any of the test groups that by using the polyfructan, the effect of reinforcing a creamy taste and texture was obtained.

By substituting the polyfructan for a part of or the whole of gelation materials, thickening agents, low calorie sugars or oils and fats, there are provided food having a good taste and flavor in which agreeability to the palate, meltability on the tongue and smooth swallowing are improved, and good gel property and creamy texture are reinforced.

TABLE 1

| Formulation of low calorie mayonnaise | | | | | |
| --- | --- | --- | --- | --- | --- |
| | Control | A | B | C | D |
| Corn salad oil | 66 | 44 | 22 | 0 | 22 |
| 25% Polyfructan paste | 0 | 22 | 44 | 66 | 0 |
| 20% Polyfructan paste | 0 | 0 | 0 | 0 | 44 |
| Yolk | 10 | 10 | 10 | 10 | 10 |
| Table salt | 1 | 1 | 1 | 1 | 1 |
| Creal vinegar | 7.5 | 7.5 | 7.5 | 7.5 | 7.5 |

TABLE 2

| Results of evaluation on low calorie mayonnaise | | | | | |
| --- | --- | --- | --- | --- | --- |
| | Control | A | B | C | D |
| Comment | strongly sour | mild | mild | pasty | mild |
| | strongly salty | spreadable | smooth | powdery | mildly sour |
| | strongly sour & salty | good meltability on the tongue | pasty | | mildly salty |
| | | mildly sour | | | good meltability on the tongue |
| Total scoring | 5.0 | 4.1 | 2.8 | 2.4 | 4.2 |

TABLE 3

| Formulation of low calorie dressing | | | | |
| --- | --- | --- | --- | --- |
| | Control | A | B | C |
| Corn salad oil | 37 | 25 | 12 | 0 |
| 20% Polyfructan paste | 0 | 12 | 25 | 37 |
| Creal vinegar | 14 | 14 | 14 | 14 |
| Granulated sugar | 4.7 | 4.7 | 4.7 | 4.7 |
| Table salt | 3.4 | 3.4 | 3.4 | 3.4 |
| Sodium glutamate | 0.4 | 0.4 | 0.4 | 0.4 |
| Xanthane gum | 0.4 | 0.4 | 0.4 | 0.4 |
| Black pepper | 0.1 | 0.1 | 0.1 | 0.1 |
| Water | 40 | 40 | 40 | 40 |

TABLE 4

| Results of evaluation on low calorie dressing | | | |
| --- | --- | --- | --- |
| | A | B | C |
| Comment | mild taste | mild taste | strong pepper flavor |
| | weakly acidic and salty | good adherence to vegetable | no oily smell |
| | good adherence to vegetable | no oily smell | light taste |

TABLE 5

| Formulation of low calorie whipped cream | | | |
| --- | --- | --- | --- |
| | Control | A | B |
| Fresh cream | 100 | 50 | 50 |
| 25% Polyfructan paste | 0 | 50 | 0 |
| 25% Polydextrose | 0 | 0 | 50 |
| Sugar | 10 | 10 | 10 |

TABLE 6

| Formulation of low calorie bavarois | | | |
| --- | --- | --- | --- |
| | Control | A | B |
| Fresh cream | 100 | 50 | 50 |
| 25% Polyfructan paste | 0 | 50 | 0 |
| Yolk | 18 | 18 | 18 |
| Granulated sugar | 40 | 40 | 40 |
| Milk | 100 | 100 | 100 |
| Gelatin | 6 | 6 | 6 |
| Vanilla essence | 0.3 | 0.3 | 0.3 |

TABLE 6-continued

Formulation of low calorie bavarois

|  | Control | A | B |
|---|---|---|---|
| Water | 30 | 30 | 30 |

TABLE 7

Formulation of low calorie chocolate cream

|  | Control | A | B | C |
|---|---|---|---|---|
| Fresh cream | 33 | 22 | 11 | 0 |
| 20% Polyfructan paste | 0 | 11 | 22 | 33 |
| Sweet chocolate | 67 | 67 | 67 | 67 |

TABLE 8

Results of evaluation on low calorie chocolate cream

|  | Control | A | B | C |
|---|---|---|---|---|
| Comment | somewhat poor meltability | light flavor; mild; good agreeability on the tongue | mild; good flower decorating property; good shape retention property | good agreeability to the palate; good flower decorating property; good shape retention property; hard chocolate-like |
| Total scoring | 5.0 | 5.8 | 5.1 | 4.1 |

TABLE 9

Formulation of low calorie souffle gras

|  | Control | A | B |
|---|---|---|---|
| Fresh cream | 50 | 25 | 25 |
| 20% Polyfructan paste | 0 | 25 | 0 |
| 20% Paselli SA-2 | 0 | 0 | 25 |
| Granulated sugar | 20 | 20 | 20 |
| Yolk | 18 | 18 | 18 |
| Gran marnier | 10 | 10 | 10 |
| Water | 15 | 15 | 15 |

TABLE 10

Low calorie cheese paste

|  | Control | A | B |
|---|---|---|---|
| Cream cheese | 100 | 50 | 25 |
| 25% Polyfructan paste | 0 | 50 | 75 |

TABLE 11

Formulation of low calorie rare cheese cake

|  | Control | A | B |
|---|---|---|---|
| Fresh cream | 160 | 80 | 80 |
| 20% Polyfructan paste | 0 | 80 | 0 |
| 20% Paselli SA-2 | 0 | 0 | 80 |
| Granulated sugar | 14 | 14 | 14 |
| Lemon juice | 7.5 | 7.5 | 7.5 |
| Gelatin | 3 | 3 | 3 |
| Water | 50 | 50 | 50 |

TABLE 12

Formulation of low calorie butter cream

|  | Control | A | B |
|---|---|---|---|
| Salt-free butter | 100 | 50 | 50 |
| 25% Polyfructan paste | 0 | 50 | 0 |
| 25% Polydextrose | 0 | 0 | 50 |
| Yolk | 21 | 21 | 21 |
| Granulated sugar | 50 | 50 | 50 |

TABLE 12-continued

Formulation of low calorie butter cream

|  | Control | A | B |
|---|---|---|---|
| Water | 18 | 18 | 18 |

TABLE 13

Formulation of low calorie baked cheese cake

|  | Control | A | B | C | D |
|---|---|---|---|---|---|
| Cream cheese | 100 | 50 | 0 | 100 | 100 |
| Fresh cream | 80 | 80 | 80 | 40 | 0 |
| 25% Polyfructan paste | 0 | 50 | 100 | 40 | 80 |
| Egg | 40 | 40 | 40 | 40 | 40 |
| Soft flour | 10 | 10 | 10 | 10 | 10 |
| Granulated sugar | 35 | 35 | 35 | 35 | 35 |

TABLE 14

Results of evaluation on low calorie baked cheese

| A | B | C | D |
|---|---|---|---|
| Mild texture; good spreadability and extendibility; no difference from control in taste and flavor; good meltability on the tongue; somewhat weakly sour. | Weak cheese flavor; creamy texture; strong flavor like egg and fresh cream; good spreadability and extendibility; good meltability on the tongue; mildly sour. | No difference from control in taste; flavor and texture; good spreadability and extendibility; rich taste; agreeable to the palate and good meltability on the tongue. | Creamy texture somewhat poor smoothness; rich taste; strong flavor like egg. |

TABLE 15

Formulation of low calorie madelaine

|  | Control | A | B | C | D |
|---|---|---|---|---|---|
| Salt-free butter | 60 | 40 | 20 | 20 | 20 |
| Granulated sugar | 60 | 60 | 60 | 60 | 60 |
| Soft flour | 60 | 60 | 60 | 60 | 70 |
| Egg | 60 | 60 | 60 | 60 | 60 |
| Water | 0 | 0 | 0 | 30 | 30 |
| 25% Polyfructan paste | 0 | 20 | 40 | 0 | 0 |

TABLE 16

Results of evaluation on low calorie madelaine

| A | B | C | D |
|---|---|---|---|
| Similar to control in appearance, texture and flavor; strong butter flavor; moist and delicious. | Somewhat white a bit sticky, strong flavor; somewhat sweet like sweet pastry. | Crispy & dry; light castilla-like; weak butter flavor; watery; strongly sweet. | Somewhat hard texture like sponge cake; strong egg flavor; weak butter flavor. |

TABLE 17

Formulation of low calorie bread

|  | Control | A | B |
|---|---|---|---|
| Soft flour | 250 | 250 | 250 |
| Granulated sugar | 34 | 34 | 34 |
| Skimmed milk | 6 | 6 | 6 |
| Table salt | 5 | 5 | 5 |
| Shortening | 30 | 20 | 10 |
| Water | 150 | 150 | 150 |
| Dry yeast | 3 | 3 | 3 |
| 25% Polyfructan paste | 0 | 10 | 20 |

TABLE 18

Results of evaluation on low calorie bread

| A | B |
|---|---|
| No difference from control in taste, flavor and texture; delicious. | Somewhat moist texture; color is somewhat light when baked; edge portion is soft. |

TABLE 19

Formulation of low calorie American pastry

| | Control | A | B |
|---|---|---|---|
| Hard flour | 55 | 55 | 55 |
| Soft flour | 20 | 20 | 20 |
| Shortening | 55 | 35 | 20 |
| Polyfructan paste | 0 | 50 | 0 |
| Chilled water | 25 | 25 | 25 |
| Table salt | 1.5 | 1.5 | 1.5 |

TABLE 20

Formulation of low calorie brioche

| | Control | A | B |
|---|---|---|---|
| Shortening | 100 | 67 | 37 |
| 25% Polyfructan paste | 0 | 33 | 67 |
| Hard flour | 100 | 100 | 100 |
| Soft flour | 100 | 100 | 100 |
| Granulated sugar | 18 | 18 | 18 |
| Skimmed milk | 6 | 6 | 6 |
| Table salt | 4 | 4 | 4 |
| Water | 40 | 40 | 40 |
| Egg | 60 | 60 | 60 |
| Dry yeast | 4 | 4 | 4 |

TABLE 21

Formulation of low calorie doughnuts

| | Control | Sample |
|---|---|---|
| Soft flour | 100 | 100 |
| Baking powder | 3 | 3 |
| Sugar | 25 | 25 |
| Shortening | 10 | 0 |
| 25% Polyfructan paste | 0 | 10 |
| Egg | 25 | 25 |
| Water | 12 | 12 |

TABLE 22

Formulation of low calorie corn potage

| | Control | A | B |
|---|---|---|---|
| Soup base | 200 | 200 | 200 |
| Milk | 100 | 100 | 100 |
| Fresh cream | 38 | 25 | 13 |
| 25% Polyfructan paste | 0 | 13 | 25 |
| Table salt | 1 | 1 | 1 |

TABLE 23

Formulation of soup base used above

| | |
|---|---|
| Corn (cream style) | 500 |
| Butter | 80 |
| Onion | 160 |
| Carrot | 100 |
| Wheat flour | 40 |
| Hot water | 1600 |
| Consomme | 2 pieces |
| | Boiled down to 1600 in total |

TABLE 24

Formulation of low calorie margarine

| | Control | A | B |
|---|---|---|---|
| Margarine blend oil | 1590 | 1060 | 530 |

TABLE 24-continued

Formulation of low calorie margarine

| | Control | A | B |
|---|---|---|---|
| 20% Polyfructan paste | 0 | 530 | 1060 |
| Lecithin | 4 | 4 | 4 |
| Monoglyceride | 6 | 6 | 6 |
| Water | 376 | 376 | 376 |
| Table salt | 24 | 24 | 24 |

TABLE 25

Formulation of yogurt beverage

| | A | B |
|---|---|---|
| Yogurt (fat content, 2.35%) | 895 | 895 |
| Cherry syrup | 80 | 80 |
| Sugar | 20 | 20 |
| Corn starch | 3 | 3 |
| Locust bean gum | 2 | 2 |
| Polydextrose | 50 | 0 |
| Polyfructan | 0 | 50 |

TABLE 26

Formulation of soup

| | A | B |
|---|---|---|
| Potato powder | 60.9 g | 60.9 g |
| Chicken powder | 6.5 | 6.5 |
| Skimmed milk | 13 | 13 |
| Table salt | 6.5 | 6.5 |
| Butter powder | 13 | 13 |
| Onion extract powder | 1.3 | 1.3 |
| White pepper | 0.13 | 0.13 |
| Celery powder | 0.013 | 0.013 |
| Laurel powder | 0.013 | 0.013 |
| Polydextrose | 130 | 0 |
| Polyfructan | 0 | 130 |
| Water | 1300 g | 1300 g |
| Total | 1500 g | 1500 g |

TABLE 27

Formulation of cocoa

| | | |
|---|---|---|
| Cocoa | 0.8% | 0.8% |
| Sugar | 3.8 | 3.8 |
| Hot water | 3.8 | 3.8 |
| Milk | 76.3 | 76.3 |
| Water | 12.0 | 12.0 |
| Polydextrose | 3.0 | 3.0 |
| Polyfructan | 0 | 3.0 |

TABLE 28

Formulation of low calorie ice cream

| | A | B | C |
|---|---|---|---|
| Coconut oil | 60 g | 60 g | 60 g |
| Skimmed milk | 80 | 80 | 80 |
| Sugar | 300 | — | — |
| Aspartame | — | 1.4 | 1.4 |
| Guar gum | 3 | 3 | 3 |
| Carrageenan | 1 | 1 | 1 |
| Locust bean gum | 2 | 2 | 2 |
| Monoglyceride | 6 | 6 | 6 |
| Vanilla essence | 4 | 4 | 4 |
| Polydextrose | — | 300 | — |
| Polyfructan | — | — | 300 |
| Water | 1544 | 1543 | 1543 |
| Total | 2000 g | 2000 g | 2000 g |

TABLE 29

Formulation of sponge cake

| | A | B | C |
|---|---|---|---|
| Egg | 3 | 3 | 3 |

TABLE 29-continued

| Formulation of sponge cake | | | |
|---|---|---|---|
| | A | B | C |
| Sugar | 150 g | 150 g | 150 g |
| Wheat flour | 100 g | 100 g | 100 g |
| Butter | 30 g | 30 g | 30 g |
| Milk | 30 g | 30 g | 30 g |
| Polydextrose | — | 60 g | — |
| Polyfructan | — | — | 60 g |
| Aspartame | — | 0.2 g | 0.2 g |

TABLE 30

| Formulation of jam | | | |
|---|---|---|---|
| | Control | A | B |
| 1) Strawberry 1/5 concentrate | 60 | 60 | 60 |
| 2) Refined sugar | 210 | 105 | — |
| 3) Polyfructan | — | 105 | 210 |
| 4) APM | — | 0.525 | 1.05 |
| 5) Water | 300 | 300 | 300 |
| 6) Citric acid (50% solution) | 3.5 | 3.5 | 3.5 |
| 7) Pectin (Hi-methoxy) | 4.0 | 4.0 | 4.0 |
| 8) Calcium lactate | 0.07 | 0.07 | 0.07 |
| Total weight (g) | 577.57 | 578.095 | 578.62 |
| Final weight (g) | 300 | 300 | 300 |

Note)
A: Polyfructan substitution rate of 50%
B: Polyfructan substitution rate of 100%
Note)
B: 25% Paste was prepared from polyfructan and moisture was evaporated off to adjust the solid weight

TABLE 31

| Evaluation immediately after preparation | | |
|---|---|---|
| Sample code | A | B |
| Scoring | 5.0 | 4.8 |

TABLE 32

| Evaluation immediately after preparation | | |
|---|---|---|
| Sample code | A | B |
| Scoring | 7.5 | 6.0 |

TABLE 33

| Formulation of jelly | | | |
|---|---|---|---|
| | Control | A | B |
| Gelatin powder | 100 | 50 | 50 |
| Water | 130 | 130 | 130 |
| Sugar | 40 | 20 | 30 |
| Grape juice | 100 | 100 | 100 |
| Lemon juice | 15 | 15 | 15 |
| Polyfructan | — | 20 | 20 |
| APM | — | 0.11 | 0.05 |

TABLE 34

| Evaluation on various desserts | | | | | | |
|---|---|---|---|---|---|---|
| Example | 30 | 31 | 32 | 33 | 34 | 35 |
| Softness | 5.5 | 7.0 | 6.0 | 5.2 | 6.6 | 5.0 |
| Smoothness | 6.5 | 6.0 | 7.3 | 6.8 | 7.5 | 6.1 |
| Spreadability | 5.8 | 5.5 | 6.4 | 5.2 | 5.9 | 5.4 |
| Creamy texture | 6.0 | 5.6 | 7.4 | 5.5 | 6.6 | 5.8 |
| Pleasantness | 6.0 | 7.0 | 6.6 | 6.3 | 6.6 | 5.8 |

What is claimed as new and desired to be secured by Letters Patent of the United States is:

1. A food or drink comprising in whole or in part, as a substitute for oil, fat, sugar, gelation material and/or thickening agent an effective amount of a fructose polymer having a molecular weight of 2,000 to 20,000,000 mainly composed of β-2,1-bonds, wherein said fructose polymer is, in whole or in part, a substitute for oil, fat, sugar, gelation material and/or thickening agent.

2. The food or drink of claim 1, wherein the fructose polymer contains β-2,6-bond as a branched chain.

3. The food or drink of claim 1, wherein the fructose was formed by incubating the conidium of *Aspergillus sydowi* and sugar or by using fructose transferase derived from yeast, *Aspergillus oryzae, Aspergillus niger, Aureoba sidium, pullulans* and sugar or inulin.

4. The food or drink of claim 1, wherein the fructose polymer has a molecular weight in the range of 10,000 to 15,000,000.

5. The food or drink of claim 1, wherein the food or drink is selected from the group consisting of spreads, sauce, low calorie mayonnaise, low calorie dressing, cream, low calorie whipped cream, low calorie chocolate cream, low calorie souffle gras, low calorie cheese paste, low calorie rar cheese cake, low calorie butter cream, low calorie baked cheese cake, low calorie madeleine, low calorie bread, low calorie American pastry, low calorie brioche, low calorie doughnuts, low calorie corn potage soup, low calorie margarine, yogurt beverage, soup, cocoa, low calorie ice cream, sponge cake, pudding, cookies, lacto-ice cream, sherbert, ice-milk, jam, jelly, custard pudding, chocolate mousse, wine cream, bavarois, ice cream, ham, and sausage of fish and meat.

6. The food or drink of claim 1 wherein the fructose polymer having been added to the food or drink is dispersed in water, milk or mixture thereof in 10 to 40% (w/w) to form a paste.

7. A method of producing a food or drink according to claim 1 with reduced oil, fat, and sugar content yet retaining good gelation properties and good organoleptic properties such as taste, texture, and flavor comprising substituting, wholly or partially, a fructose polymer having a molecular weight of 2,000 to 20,000,000 mainly composed of β-2,1-bonds for oils, fats, oil and fat substitutes, thickening agents, gelation materials, and low calorie sugars present in said food or drink.

8. The method according to claim 7, wherein 20 to 70% by weight of the oils and fats are substituted by said fructose polymer.

9. The method according to claim 7, wherein the fructose polymer is used in the form of a powder or a fluid.

10. The method according to claim 9, wherein the fructose polymer is used in the form of a paste by dispersing the fructose polymer in water, milk, other raw material of the food or drink, or mixture thereof and the desired hardness of the paste is adjusted by controlling the amount of fructose polymer in water, milk, other raw material of the food or drink, or mixture thereof.

11. The method according to claim 10, wherein the fructose polymer is dispersed in water, milk, other raw material of the food or drink, or mixture thereof in 10 to 40% (w/w).

12. The method according to claim 7, wherein the degree of substitution of the form of fructose polymer for the gelation material or thickening agent or the ratio of the form of fructose polymer to gelation material or thickening agent is determined by the desired degree of gelation.

13. An oil or fat substitute comprising a fructose polymer having a molecular weight of 2,000 to 20,000,000 mainly composed of β-2,1-bonds disposed in water, milk, other raw material of a food or drink, or mixture thereof.

14. A sugar substitute comprising a fructose polymer having a molecular weight of 2,000 to 20,000,000 mainly composed of β-2,1-bonds and a sweetener having a high degree of sweetness.

15. The sugar substitute of claim 14, wherein the sweetener having a high degree of sweetener is aspartame.

16. A food comprising, in whole or in part, as a substitute for at least one of a gelation material, a thickening agent, a low calorie sugar, a sweetener having a high degree of sweetness, and an oil and fat, an effective amount of a fructose polymer having a molecular weight of 2,000 to 20,000,000 mainly composed of β-2,1-bonds, wherein said fructose polymer is a substitute for a part of or the whole of the gelation material, the thickening agent, the low calorie sugar and the oil and fat.

17. The food according to claim 16, wherein said oil and fat is at least one selected from the group consisting of fresh cream, cream cheese, butter and a vegetable oil.

18. The food according to claim 16, wherein said gelation material and/or thickening agent is at least one selected from the group consisting of gelatin, a gum substance, pectin, starch, yolk and albumen.

19. The food or drink according to any one of claims 1 through 3, wherein said food or drink contains cream, jelly, bavarois, mousse, jam, ice cream, ice milk, lacto-ice cream, sherbet, sauce, mayonnaise, dressing, white sauce, chocolate, pudding, sponge cake, break, spread, butter, margarine, ham or sausage of fish and meat.

20. The food according to claim 14, wherein said sweetener having a high degree of sweetness is aspartame.

* * * * *